United States Patent [19]

Czech

[11] Patent Number: 5,433,892

[45] Date of Patent: Jul. 18, 1995

[54] ELECTRICALLY CONDUCTIVE TRANSPARENT PRESSURE-SENSITIVE ADHESIVE FILMS; PROCESS FOR THEIR PRODUCITON; AND THEIR USE IN THE PRODUCTION OF MIOMEDICAL ELECTRODES

[75] Inventor: Zbigniew Czech, Koblenz, Germany

[73] Assignee: Lohmann GmbH & Co. KG, Neuwied, Germany

[21] Appl. No.: 70,470

[22] PCT Filed: Dec. 5, 1991

[86] PCT No.: PCT/EP91/02318

§ 371 Date: Jun. 2, 1993

§ 102(e) Date: Jun. 2, 1993

[87] PCT Pub. No.: WO92/10553

PCT Pub. Date: Jun. 25, 1992

[30] Foreign Application Priority Data

Dec. 13, 1990 [DE] Germany .................. 40 39 780.7

[51] Int. Cl.$^6$ .................. H01B 1/00; A61B 5/04
[52] U.S. Cl. .................. 252/500; 252/518; 252/62.2; 128/640; 523/105; 523/111; 428/320.2; 428/411.1; 428/913
[58] Field of Search .................. 252/500, 518, 622; 128/640; 523/105, 111; 428/320.2, 411.1, 913

[56] References Cited

U.S. PATENT DOCUMENTS

| 4,273,135 | 6/1981 | Larimore et al. | 128/640 |
| 4,352,359 | 10/1982 | Larimore et al. | 128/640 |
| 4,391,278 | 7/1983 | Cahalan et al. | 128/640 |
| 4,524,087 | 6/1985 | Engel | 427/2 |
| 4,777,954 | 10/1988 | Keusch et al. | 128/640 |

FOREIGN PATENT DOCUMENTS

| 0177139 | 4/1986 | European Pat. Off. . |
| 0263586 | 4/1988 | European Pat. Off. . |
| 0322098 | 6/1989 | European Pat. Off. . |
| 1594137 | 10/1970 | Germany . |

Primary Examiner—Paul Lieberman
Assistant Examiner—M. Kopec
Attorney, Agent, or Firm—Collard & Roe

[57] ABSTRACT

The invention concerns an electrically conductive, transparent, pressure-sensitive adhesive film with an electric conductivity above $10^{-5}$ S, for the production of biomedical electrodes, consisting of 100 parts by weight of a carboxyl group-containing copolymer on an acrylate basis;

50 to 150 parts by weight of a water-soluble amine;

50 to 250 parts by weight of a polyoxyalkylene with a molecular mass of below 1000 and/or a polyalcohol and/or its derivatives;

50 to 200 parts by weight of a solution of electrolytes and 0.1 to 6 parts by weight of a cross-linking agent.

14 Claims, No Drawings

ELECTRICALLY CONDUCTIVE TRANSPARENT PRESSURE-SENSITIVE ADHESIVE FILMS; PROCESS FOR THEIR PRODUCITON; AND THEIR USE IN THE PRODUCTION OF MIOMEDICAL ELECTRODES

The invention concerns electrically conductive transparent pressure-sensitive adhesive films with an electric conductivity above $10^{-5}$ S, suitable for the production of biomedical electrodes.

The popular, conventional design of such biomedical electrodes comprises an electrically conductive gel in a hole punched out of foamed material, whose storage life is limited owing to the drying-out which increasingly occurs as the period of storage progresses. A further disadvantage of this drying-out is that the skin has to be cleansed from remainders of the gel after the electrodes have been used and that the patient's clothing may become soiled if the remainders of the gel are not removed carefully enough. Efforts were, therefore, made to eliminate or substantially reduce these disadvantages, by providing a pressure-sensitive adhesive coating, stable in storage and geared for electric conductivity.

Conventional methods for the realization of electric conductivity, such as, for example, the incorporation of graphite powder, are not practical, as the pressure-sensitive adhesive film has to remain transparent.

According to DE-OS 15 94 137, pressure-sensitive adhesive conductive strips are known which contain film-forming ionized organic polymer salts. The polymers themselves are only slightly soluble in water, but are rendered hydrophilic and ionogenic by the built-in functional groups, which are capable of forming salts. The sodium salts of sulphonated styrene and polybenzyl sulphonate can be cited as suitable examples. A further preferred group are the salts of quaternary polymers from dimethylaminoethyl methacrylate or its copolymers with butyl acrylate and 4-vinyl pyridine, that has been 95 to 100% quaternized with methyl bromide or allyl chloride.

According to EP-A 0 263 586, conductive pressure-sensitive adhesives from a hydrogen-donor monomer (e.g. acrylic acid) and a hydrogen-acceptor monomer (e.g. N-vinyl pyrrolidone) are used to produce electrically conductive pressure-sensitive adhesive films.

A mixture of water and glycerine is used as the polymerization medium. A water-soluble salt and—as a cross-linking agent—bifunctional (meth)acrylate are also added to the copolymer.

In EP-A 0 322 098 a production of electrically conductive pressure-sensitive adhesive films is described in which a hydrophilic pressure-sensitive adhesive based on N-vinyl lactam is used, mixed with a softening agent and cross-linked with multifunctional derivatives that have not been saturated with ethylene.

When used to produce biomedical electrodes, however, these known pressure-sensitive adhesive films exhibit a number of shortcomings, which restrict their practical application. Their power of cohesion is reduced, due to their sensitivity to the moisture of the skin. After they have been in contact with the skin for several hours, traces of adhesive remain on the skin when they are peeled off, making the reuse of such biomedical electrodes equipped with these electrically conductive pressure-sensitive adhesive films impossible.

The task forming the basis of the invention in question is thus that of producing electrically conductive pressure-sensitive adhesive films which manifest excellent resistance to moisture and stable inner strength and which are exceptionally suitable for the production of reusable biomedical electrodes.

The problem underlying the invention is solved surprisingly by electrically conductive transparent pressure-sensitive adhesive films with an electric conductivity above $10^{-5}$ S, consisting of 100 parts by weight of a copolymer containing a carboxyl group, on an acrylate basis; 50 to 150 parts by weight of a water-soluble amine; 50 to 250 parts by weight of polyoxyalkylene with a molecular mass of below 1000 and/or a polyalcohol and/or its derivatives; 50 to 200 parts by weight of a solution of electrolytes; and 0.1 to 6 parts by weight of a cross-linking agent.

The favoured carboxyl group-containing copolymers on an acrylate basis are synthesized, preferably by means of a radical solvent polymerization of a) 40 to 80 weight percent of alkyl(meth)acrylates with 4 to 12 C-atoms in the alkyl radical b) 10 to 30 weight percent of hydroxyl group-containing (meth)acrylates c) 5 to 30 weight percent of monoethenoid carboxylic acids d) 0.5 to 20 weight percent of salts of unsaturated organic sulphonic acids e) 0.1 to 5 weight percent of salts of N-substituted carboxyl group-containing (meth)acrylamide derivatives.

Butyl, pentyl, hexyl, heptyl, octyl, 2-ethylhexyl, isooctyl, 2-methylheptyl, nonyl, isononyl, decyl or dodecyl(meth)acrylate are preferred as alkyl(meth)acrylates with 4 to 12 carbon atoms in the alkyl radical.

The hydroxyalkyl(meth)acrylates and, in particular, 2-hydroxyethyl(meth)acrylate, 2-hydroxypropyl(meth)acrylate or 4-hydroxybutyl(meth)acrylate, are favoured as hydroxyl group-containing (meth)acrylates; they can be used on their own or in a mixture with one another.

Favoured vinyl carboxylic acids, which form active cross-linking centres in the finished polymer, are (meth)acrylic acid, $\beta$-acryloyloxy propionic acid, vinyl acetic acid, aconitic acid, trichlor acrylic acid, dimethyl acrylic acid, crotonic acid, fumaric acid or itaconic acid. (Meth)acrylic acid and $\beta$-acryloyloxy propionic acid are particularly favoured.

The salts of the unsaturated organic sulphonic acids, which are used in the production of the carboxyl group-containing copolymers on an acrylate basis, are preferably metallic salts, especially alkali metal and/or ammonium salts, the salts of vinyl sulphonic acid, 2-methyl-prop-1-en-3-sulphonic acid, vinylbenzyl sulphonic acid and 2-acrylamido-2-methylpropane sulphonic acid being preferred. Lithium, sodium and/or potassium salts are particularly suited as metallic salts.

N-substituted (meth)acrylamide derivatives with the general formula

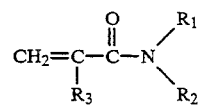

are preferably used as known N-substituted, carboxyl group-containing (meth)acrylamide derivatives. $R_1$ can be a hydrogen atom, an alkyl, aryl, arylalkyl, alkylaryl, alkoxyalkyl, alkoxyaryl, acetylalkyl or acetylalkoxyalkyl group; $R_2$ a carboxyalkyl or carboxylaryl group; and $R_3$ a hydrogen atom or a methyl group. The alkali or ammonium salts are particularly suitable as the salts of these compounds.

The carboxyl group-containing copolymer is applied, together with a water-soluble amine. Water-soluble polyoxyalkylene amines with the general formula

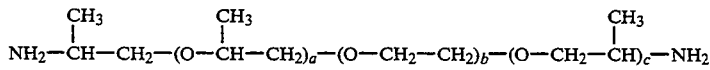

in which a+c is larger than 2, and b is larger than 6 and smaller than 60.

Polyethylene glycols, polypropylene glycols, polyoxypropylene/polyoxyethylene copolymers, monoethylene glycol dimethylether or polyethylene glycol dimethylether are employed as polyoxyalkylenes with a molecular mass of below 1000.

Glycerine or its derivatives such as diacetin, glyceric aldehyde, glyceric acid, glyceric acid methylester, α-monoacetin or α-monobutyrin are preferred as polyalcohols.

A solution of electrolytes (an aqueous solution of organic or anorganic salts) is added to the copolymer, in order to attain the required electrical conductivity of the pressure-sensitive adhesive on an acrylate basis. An aqueous NaCl or KCl solution regarded as being physiologically safe is particularly favoured.

Metallic chelates, esters of metallic acids, epoxy, aziridine or melamine formaldehyde resins are recommended as suitable cross-linking agents, capable of forming an intermolecular structure with the carboxyl groups. Cross-linking agents which react at room temperature, such as, for example, metallic chelates, are particularly suitable.

The carboxyl group-containing copolymer on an acrylate basis, is synthesized from the required components by means of radical polymerization in the solvent in a way which is known. The polymer obtained is stabilized with isopropyl alcohol and mixed with a water-soluble amine, polyoxyalkylene or polyalcohol, an aqueous solution of electrolytes and a cross-linking medium. The pressure-sensitive adhesive thus obtained is applied to a siliconized sheet, dried in a drying tunnel at 65° C. and then worked into an electrically conductive pressure-sensitive adhesive article by laminating it to a suitable substrate.

The invention will be described in more detail using the following examples.

EXAMPLES 1–10

The abbreviations employed in the following table have the following meaning:

Index of Abbreviations

2-EHA—2-ethylhexyl acrylate
IO—Isooctyl acrylate
BA—Butyl acrylate
HEA—2-hydroxyethyl acrylate
HPA—2-hydroxypropyl acrylate
HBA—4-hydroxybutyl acrylate
AA—Acrylic acid
APA—β-acryloyloxy propionic acid
VS-Na—Sodium vinyl sulphonate
MAS-Na—Sodium methallyl sulphonate
AMBA-Na—Sodium salt of the 3-acrylamido-3-methylbutyric acid
AHA-Na—Sodium salt of the 10-acrylamido-hendecane acid
ED 600—Polyoxyalkylene amine with a molecular mass of 600
ED 900—Polyoxyalkylene amine with a molecular mass of 900
PEG 200—Polyethylene glycol with a molecular mass of 200
PPG 405—Polypropylene glycol with a molecular mass of 405
AlACA—Aluminium acetyl acetonate
ZrACA—Zircon acetyl acetonate The polymers formed by solution polymerization from the monomers listed in Table 1 have a solids content of ca. 50 weight percent.

After the polymers produced in this manner have been diluted with isopropyl alcohol until a solids content of 33 weight percent is reached, the solution of polimerides is mixed with the components which can be seen in Table 2, such as water-soluble amine, polyoxyalkylene or polyalcohol, a solution of electrolytes and cross-linking agents. The pressure-sensitive adhesives obtained in this way are applied to a siliconized polyester sheet, dried for 10 minutes in a drying tunnel and subsequently covered with an aluminized polyester sheet. The thickness of the adhesive was ca. 140 g/m².

The finished product was conditioned for a week at room temperature.

The electric conductivity of the transparent pressure-sensitive adhesive films was measured, using a high-resistance measuring instrument in accordance with DIN 53 482.

TABLE 1

| | Composition of Polymerization weight percent | | | | | | | | | | | |
|---|---|---|---|---|---|---|---|---|---|---|---|---|
| | C4–C12 Alkyl(meth)acrylate | | | hydroxyl group-containing (Meth)acrylate | | | Vinyl carboxylic acid | | Sulfonic acid | | salts of the carboxyl group-containing N-substituted (meth)acrylamid derivatives | |
| Example | 2-EHA | IO | BA | HEA | HPA | HBA | AA | APA | VS-Na | MAS-Na | AMBA-Na | AHA-Na |
| 1 | 30 | — | 30 | 10 | — | — | 25 | — | 3 | — | 1 | — |
| 2 | 60 | — | — | 15 | — | — | 20 | — | — | 3 | — | 2 |
| 3 | 60 | 17 | — | — | 20 | — | 20 | — | 1 | — | 2 | — |
| 4 | 10 | 36 | 18 | — | — | 15 | 10 | 5 | — | 5 | — | 1 |
| 5 | — | — | 50 | — | 18 | — | 30 | — | — | 1 | — | 1 |
| 6 | — | 17 | 40 | — | 15 | — | — | 15 | 10 | — | 3 | — |
| 7 | 47 | — | 10 | 5 | — | 10 | 10 | 10 | 7 | — | 1 | — |

TABLE 1-continued

| | Composition of Polymerization weight percent | | | | | | | | | | |
|---|---|---|---|---|---|---|---|---|---|---|---|
| | C4–C12 Alkyl(meth)acrylate | | | hydroxyl group-containing (Meth)acrylate | | | Vinyl carboxylic acid | | Sulfonic acid | | salts of the carboxyl group-containing N-substituted (meth)acrylamid derivatives |
| Example | 2-EHA | IO | BA | HEA | HPA | HBA | AA | APA | VS-Na | MAS-Na | AMBA-Na | AHA-Na |
| 8 | 23 | — | 23 | — | 30 | — | 20 | — | — | 2 | — | 2 |
| 9 | — | 60 | — | 5 | 10 | — | — | 10 | 12 | — | 3 | — |
| 10 | 40 | 14,5 | — | — | 15 | — | 25 | — | 5 | — | — | 0,5 |

TABLE 2

| Example | Polymeride [parts by weight] | water-soluble amine [parts by weight] | | Polyoxyalkylene or Polyol [parts by weight] | | | solution of electrolytes [parts by weight] | | | crosslinking agent [parts by weight] | | electric conductivity [S] |
|---|---|---|---|---|---|---|---|---|---|---|---|---|
| | | ED 600 | ED 900 | PEG 200 | Glycerin | PPG 405 | 15%-NaCl solution | 20%-NaCl solution | 15%-KCl solution | AlACA | ZrACA | |
| 1 | 100 | 100 | — | 50 | 100 | — | 100 | — | — | 1,5 | — | >10⁻⁵ |
| 2 | 100 | — | 120 | 50 | — | 70 | — | 150 | — | — | 0,8 | >10⁻⁵ |
| 3 | 100 | 80 | — | — | 200 | — | — | — | 120 | 0,5 | 0,5 | >10⁻⁵ |
| 4 | 100 | 100 | 10 | — | — | 220 | 100 | — | 80 | 2,0 | — | >10⁻⁵ |
| 5 | 100 | 90 | — | — | — | 150 | 100 | — | 100 | 0,9 | — | >10⁻⁵ |
| 6 | 100 | — | 100 | — | 50 | 70 | — | 80 | — | 2,5 | — | >10⁻⁵ |
| 7 | 100 | 50 | 50 | 100 | — | — | — | — | 150 | — | 0,6 | >10⁻⁵ |
| 8 | 100 | 150 | — | — | 150 | — | — | 100 | — | 2 | — | >10⁻⁵ |
| 9 | 100 | 120 | — | 120 | — | — | — | 150 | — | — | 1,0 | >10⁻⁵ |
| 10 | 100 | — | 90 | — | — | 200 | — | — | 150 | — | 1,5 | >10⁻⁵ |

As can be seen from Table 1, the measured conductivity was in all cases above $10^{-5}$ S, which means that the pressure-sensitive adhesive films are especially suitable for the production of biomedical electrodes.

When such pressure-sensitive adhesive films are peeled off the skin, no remainders of adhesive are left on the skin, thus making it possible to reuse the biomedical electrodes provided with these electrically conductive pressure-sensitive adhesive films.

EXAMPLE 11

For the production of an electrically conductive electrode, the electrically conductive pressure-sensitive adhesive film, which had been produced using the pressure-sensitive adhesive mass synthesized according to example 1, was transferred onto a polyethylene foam. Located between the polyethylene foam and the electrically conductive pressure-sensitive adhesive film laminated thereon were a number of parallel electrode strips with a short, ca. 40 cm-long connecting cable. The contact surface measured 40×40 mm.

I claim:
1. Electrically conductive, transparent, pressure-sensitive adhesive film with an electric conductivity above $10^{-5}$ S, consisting of
   100 parts by weight of a carboxyl group-containing copolymer on an acrylate basis, said carboxyl group-containing copolymer, comprising 10 to 30 weight percent of hydroxyl group-containing (meth) acrylates;
   50 to 150 parts by weight of a water-soluble amine;
   50 to 250 parts by weight of a polyoxyalkylene with a molecular mass of below 1000, a polyalcohol, its derivatives and mixtures thereof;
   said polyoxyalkylene with a molecular mass below 1000 being selected from the group consisting of polyethylene glycol, polypropylene glycol, polyoxypropylene/polyoxyethylene copolymers, monoethylene glycol dimethyl ether, and polyethylene glycol dimethyl ether, and that the polyalcohol is glycerine or a derivative thereof selected from the group consisting of diacetin, glyceric aldehyde, glyceric acid, glyceric acid methyl-ester, α-monoacetin, and α-monobutyrin;
   50 to 200 parts by weight of a solution of electrolytes; and
   0.1 to 6 parts by weight of a cross-linking agent.

2. Pressure sensitive adhesive film according to claim 1, wherein the carboxyl group-containing copolymer further consists of
   a) 40 to 80 weight percent of alkyl (meth)acrylates with 4 to 12 C-atoms in the alkyl radical,
   b) 5 to 30 weight percent of monoethenoid carboxylic acids,
   c) 0.5 to 20 weight percent of salts of unsaturated organic sulphonic acids, and
   d) 0.1 to 5 weight percent of salts of carboxyl group-containing, N-substituted (meth)acrylamide derivatives.

3. Pressure-sensitive adhesive film according to claim 2, characterized in that the alkyl(meth)acrylate with 4 to 12 C-atoms in the alkyl radical is a butyl, pentyl, hexyl, heptyl, octyl, 2-ethylhexyl, isooctyl, 2-methylheptyl, nonyl, decyl or dodecyl(meth)acrylate.

4. Pressure-sensitive adhesive film according to claim 1, characterized in that the hydroxyl group-containing (meth)acrylate is a 2-hydroxyethyl(meth)acrylate, a 2-hydroxypropyl(meth)acrylate or a 4-hydroxybutyl(meth)acrylate.

5. Pressure-sensitive adhesive film according to claim 2, characterized in that the monoethenoid carboxylic acid is selected from (meth)acrylic acid, β-acryloyloxypropionic acid, vinyl acetic acid, fumaric acid, crotonic acid, aconitic acid, dimethyl acrylic acid or itaconic acid.

6. Pressure-sensitive adhesive film according to claim 2, characterized in that the salts of the unsaturated organic sulphonic acid are alkali or ammonium salts.

7. Pressure-sensitive adhesive film according to claim 2, characterized in that the unsaturated organic sulphonic acid is a vinyl sulphonic acid, a 2-methylprop-1-en-3-sulphonic acid, a vinylbenzyl sulphonic acid or a 2-acrylamido-2-methylpropane sulphonic acid.

8. Pressure-sensitive adhesive film according to claim 2, characterized in that the salts of the carboxyl group-containing N-substituted (meth)acrylamide derivatives are alkali or ammonium salts.

9. Pressure-sensitive adhesive film according to claim 2, characterized in that the carboxyl group-containing N-substituted (meth)acrylamide derivative has the general formula

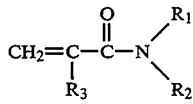

in which $R_1$ can be a hydrogen atom, an alkyl, aryl, arylalkyl, alkylaryl, alkoxyalkyl, alkoxyaryl, acetylalkyl or acetylalkoxyalkyl group; $R_2$ a carboxyalkyl or carboxylaryl group; and $R_3$ a hydrogen atom or a methyl group.

10. Pressure-sensitive adhesive film according to claim 1, characterized in that the water-soluble amine is a polyoxyalkylene amine, with the general formula

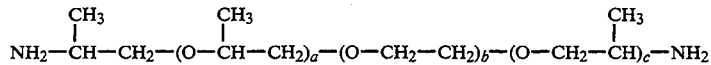

in which $a+c$ is larger than 2 and b is larger than 6 and smaller than 60.

11. Pressure-sensitive adhesive film according to claim 1, characterized in that the solution of electrolytes is a physiologically safe, aqueous, organic or inorganic salt solution.

12. Pressure-sensitive adhesive film according to claim 1, characterized in that the cross-linking agent is a metallic chelate, metallic acid ester, an epoxide, an aziridine, a triazidine or a melamine formaldehyde resin.

13. Process for the production of a pressure-sensitive adhesive film comprising the steps of (1) mixing and homogenizing 100 parts by weight of a carboxyl group-containing copolymer on an acrylate basis, obtained in solution in a way which is known, by means of polymerization, and stabilized with isopropyl alcohol, said carboxyl group-containing copolymer consisting of 10 to 30 weight percent of hydroxyl group-containing (meth)acrylates;

50 to 150 parts by weight of a water-soluble amine, 50 to 250 parts by weight of a solution of a polyoxyalkylene with a molecular mass of below 1000, a polyalcohol, its derivatives, and mixtures thereof;

said polyoxyalkylene with a molecular mass below 1000 being selected from the group consisting of polyethylene glycol, polypropylene glycol, polyoxypropylene/polyoxyethylene copolymers, monoethylene glycol dimethyl ether and polyethylene glycol dimethyl ether, and that the polyalcohol is glycerine or a derivative thereof selected from the group consisting of diacetin, glyceric aldehyde, glyceric acid, glyceric acid methyl-ester, α-monoacetin and α-monobutyrin;

50 to 200 parts by weight of a solution of electrolytes and 0.1 to 6 parts by weight of a cross-linking agent applying the homogenous pressure-sensitive adhesive mass thus obtained to a sheet whose surface has been treated, if necessary, dried and cut to the required size.

14. Use of the electrically conductive, transparent, pressure-sensitive adhesive films according to claim 1 for the production of biomedical electrodes.

* * * * *